(12) United States Patent
Itoh

(10) Patent No.: US 7,227,622 B2
(45) Date of Patent: *Jun. 5, 2007

(54) METHOD AND APPARATUS FOR SENSING BLOOD SAMPLE CONTAINED IN SAMPLE CONTAINER

(75) Inventor: Teruaki Itoh, Kumamoto (JP)

(73) Assignee: IDS Company, Ltd., Kumamoto (JP)

( * ) Notice: Subject to any disclaimer, the term of this patent is extended or adjusted under 35 U.S.C. 154(b) by 133 days.

This patent is subject to a terminal disclaimer.

(21) Appl. No.: 11/080,532

(22) Filed: Mar. 16, 2005

(65) Prior Publication Data

US 2005/0205788 A1   Sep. 22, 2005

(30) Foreign Application Priority Data

Mar. 22, 2004   (JP) .............................. 2004-083110

(51) Int. Cl.
*G01N 33/48*   (2006.01)
(52) U.S. Cl. ...................... 356/39; 422/63; 422/82.05; 422/73
(58) Field of Classification Search ................. 356/39, 356/5.01; 250/343, 357.1, 330, 332; 422/63, 422/82.05, 73, 82.01; 235/375; 436/69, 436/149
See application file for complete search history.

(56) References Cited

U.S. PATENT DOCUMENTS

| 5,286,959 A | * | 2/1994 | Demachi | ............... 235/462.14 |
| 2005/0180884 A1 | * | 8/2005 | Itoh | ........................... 422/63 |

FOREIGN PATENT DOCUMENTS

| JP | 2002-323479 | 11/2002 |
| JP | 2003-0072711 | 9/2003 |
| WO | WO 03/065007 A2 | 8/2003 |

* cited by examiner

*Primary Examiner*—Layla G. Lauchman
*Assistant Examiner*—Tri Ton
(74) *Attorney, Agent, or Firm*—Nixon & Vanderhye P.C.

(57) ABSTRACT

A blood sample contained in a sample container is separated into a serum and a clot by a separating medium. An apparatus for sensing the blood sample includes a first sensing unit which senses the separating medium using an infrared sensor and outputs a first sensing signal, a second sensing unit which senses the serum and the clot using an infrared sensor and outputs a second sensing signal, a driving unit which moves the first sensing unit and the second sensing unit relative to the sample container, a position sensing unit which outputs a position sensing signal indicating a position of the first sensing unit and a position of the second sensing unit, and a controller which calculates positions of the separating medium, the serum and the clot in response to the first sensing signal, the second sensing signal and the position sensing signal.

14 Claims, 2 Drawing Sheets

METHOD AND APPARATUS FOR SENSING BLOOD SAMPLE CONTAINED IN SAMPLE CONTAINER

CROSS-REFERENCE TO RELATED APPLICATIONS

This application is based upon and claims the benefit of priority from prior Japanese Patent Application No. 2004-083110, filed Mar. 22, 2004, the entire contents of which are incorporated herein by reference.

BACKGROUND OF THE INVENTION

1. Field of the Invention

The present invention relates to a method and an apparatus for sensing a blood sample contained in a sample container.

2. Description of the Related Art

In order to separate blood into a serum and a clot accurately using a centrifuge or the like, a test tube 1 containing a silicon-separating medium B is used. If the blood in the test tube 1 is centrifuged, it is separated into a serum A and a clot C by the silicon-separating medium B, and air D is sealed in between the serum A and a stopper 2. A blood sample is thus obtained in the test tube 1 as shown in FIG. 1.

When the above blood sample is processed to aliquot the serum A in the test tube 1 by sticking a nozzle of an aliquot/pipette instrument into the stopper 2 to reach the serum A, it is required to sense the following: separation positions of the blood sample, i.e., position e of separation between air D and serum A, position f of separation between serum A and silicon-separating medium B and position g of separation between clot C and silicon-separating medium B, separation ranges of height d of air D, height a of serum A and height b of silicon-separating medium B, and height h of stopper 2.

The air D, serum A and silicon-separating medium B differ in height and their heights d, a, and b vary with the amount of the blood sample in the test tube 1. If these heights are not sensed accurately, the following problems will occur: the nozzle of the aliquot/pipette instrument contacts the silicon-separating medium B and sucks it up, and the nozzle stops in the middle position of the serum A to leave the serum A on the top of the silicon-separating medium B.

A blood sample sensing apparatus as described above is disclosed in Jpn. Pat. Appln. KOKAI Publication No. 2002-323479. In this apparatus, a sensing coil is fitted into a test tube 1 that contains a serum A and a clot C separated by a silicon-separating medium B. The sensing coil moves relative to the test tube 1 while being supplied with a measurement signal having a given frequency. A position between the serum A and clot C is sensed based on the level variations of the measurement signal.

The sensing apparatus disclosed in the above Publication adopts a magnetic sensing means using a sensing coil. It is thus difficult to sense respective separation positions of a blood sample, respective separation ranges of height d of air D, height a of serum A and height b of silicon-separating medium B, and height h of stopper 2. The above sensing apparatus also has problems in that its configuration is complicated and its costs become high.

BRIEF SUMMARY OF THE INVENTION

In accordance with one embodiment of the present invention, there is provided a method for sensing respective separation positions and separation ranges of a blood sample with high precision and an apparatus for doing the same with simple configuration.

An apparatus for sensing a blood sample, comprises a sample container which contains a blood sample that is separated into a serum and a clot by a separating medium, a first sensing unit which senses the separating medium using an infrared sensor and outputs a first sensing signal, a second sensing unit which senses the serum and the clot using an infrared sensor and outputs a second sensing signal, a driving unit which moves the first sensing unit and the second sensing unit relative to the sample container, a position sensing unit which outputs a position sensing signal indicating a position of the first sensing unit and a position of the second sensing unit, and a controller which calculates positions of the separating medium, the serum and the clot in response to the first sensing signal, the second sensing signal and the position sensing signal.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the present invention will be described with reference to the accompanying drawings.

(Configuration of First Embodiment)

Figure 1:
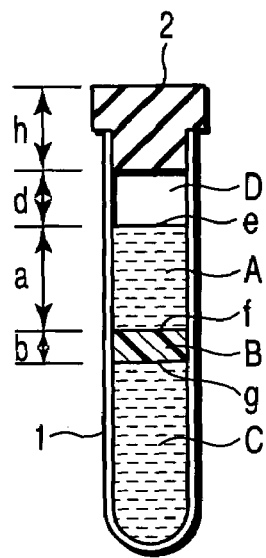
FIG. 1 is an illustration of the internal state of a conventional test tube that contains a separated blood sample.
Figure 2:
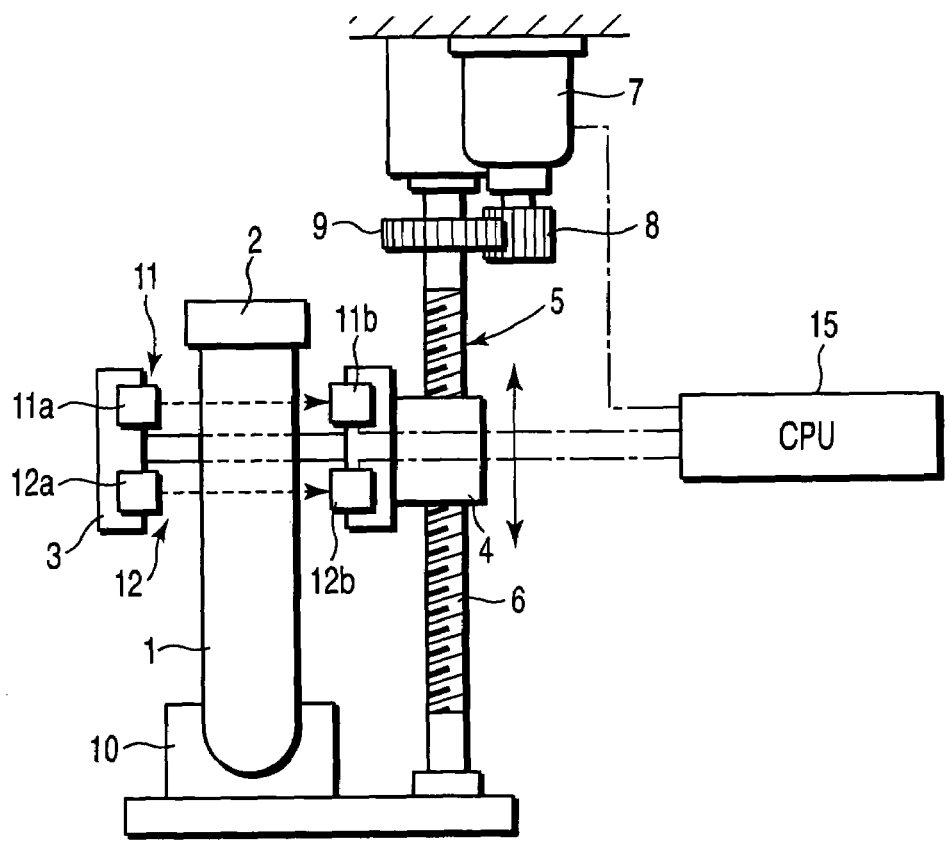
FIG. 2 is a diagram showing a configuration of a sensing apparatus according to a first embodiment of the present invention, which senses a blood sample contained in a test tube.

FIG. 2 shows a blood sample sensing apparatus according to a first embodiment of the present invention. A test tube 1 contains a blood sample to be sensed. As shown in FIG. 1, in the test tube 1, the blood sample is separated into a serum A and a clot C by a silicon-separating medium B, and air D is sealed in between the serum A and a stopper 2. A test tube holding stage 10 is a holding unit for holding the test tube 1 vertically.

Referring to FIG. 2, first and second sensing units 11 and 12 are arranged at different levels in the vertical direction of the test tube 1. The first sensing unit 11, which is located higher than the second sensing unit 12, includes an infrared ray radiation element 11a that radiates infrared rays and an infrared ray reception element 11b that receives infrared rays from the element 11a. These elements 11a and 11b face each other with the test tube 1 therebetween. The elements 11a and 11b are held by their respective element holding members 3. As the members 3 move up and down, the elements 11a and 11b move up and down at a constant speed so that the first sensing unit 11 can sense the stopper 2 and the silicon-separating medium B. The first sensing unit 11 is, for example, an infrared sensor for radiating and receiving infrared rays whose wavelength ranges from 600 nm to 800 nm and for sensing the stopper 2 and the silicon-separating medium B.

The second sensing unit 12 is located lower than the first sensing unit 11. The unit 12 includes an infrared ray radiation element 12a that radiates infrared rays which differ in wavelength from those of the first sensing unit 11 and an infrared ray reception element 12b that receives infrared rays from the element 12a. These elements 12a and 12b also face each other with the test tube 1 therebetween. The elements 12a and 12b are held by the element holding members 3, respectively. As the members 3 move up and down, the elements 12a and 12b move up and down at a constant speed together with the first sensing unit 11 so that the second sensing unit 12 can sense the air D, the serum A and the clot C. The second sensing unit 12 is, for example, an infrared sensor for radiating and receiving infrared rays whose wavelength ranges from 1400 nm to 1700 nm and which reacts on the molecules of water, and sensing the air D, the serum A and the clot C.

A driving unit 5 moves the element holding members 3 of the first and second sensing units 11 and 12 up and down so as to slide along a vertical guide (not shown). The driving unit 5 includes a screw shaft 6, a driving motor 7 and reduction gears 8 and 9. The screw shaft 6 is inserted into a screw piece 4 of the element holding member 3 and its top and bottom ends are supported such that it can rotate on its axis. The driving motor 7 adopts a stepping motor, a servo motor or the like and rotates forward and backward. The reduction gears 8 and 9 reduce the rotation of the driving motor 7 and transmit it to the screw shaft 6.

An arithmetic unit 15 is electrically connected to the driving motor 7 and the infrared ray reception elements 11b and 12b of the first and second sensing units 11 and 12. The unit 15 includes, for example, a memory as a storage unit. The unit 15 processes sensing signals of the serum A, the clot C and the silicon-separating medium B, which are output from the infrared ray reception elements 11b and 12b when they sense the serum A, the clot C and the silicon-separating medium B, and a position (height) sensing signal supplied from the driving motor 7. Thus, the unit 15 calculates respective separation positions e, f and g of the blood sample in the test tube 1 respective separation ranges of height d of air D height a of serum A and height b of silicon-separating medium B, and height h of the stopper 2, and stores these information items in the memory.

(Operation and Advantages of the Embodiment)

A method of sensing a position of a blood sample using a sensing apparatus having a configuration as described above will be described with reference to FIG. 2. A sample-contained test tube 1 is conveyed to the sensing apparatus by a conveyor unit such as a conveyor belt (not shown). Then, the test tube 1 is moved to the test tube holding stage 10 of the sensing apparatus by a robot arm (not shown) and held thereon vertically. At this time, the element holding members 3 of the first and second sensing units 11 and 12 move up and stop in the uppermost position.

As the driving motor 7 rotates in the forward direction, the screw shaft 6 rotates in the same direction and the first and second sensing units 11 and 12 move down at a constant speed. The infrared ray radiation element 11a of the first sensing unit 11 radiates infrared rays having a wavelength of 600·nm to 800 nm toward the infrared ray reception element 11b, while the infrared ray radiation element 12a of the second sensing unit 12 radiates infrared rays having a wavelength of 1400 nm to 1700 nm toward the infrared ray reception element 12b.

Figure 5:
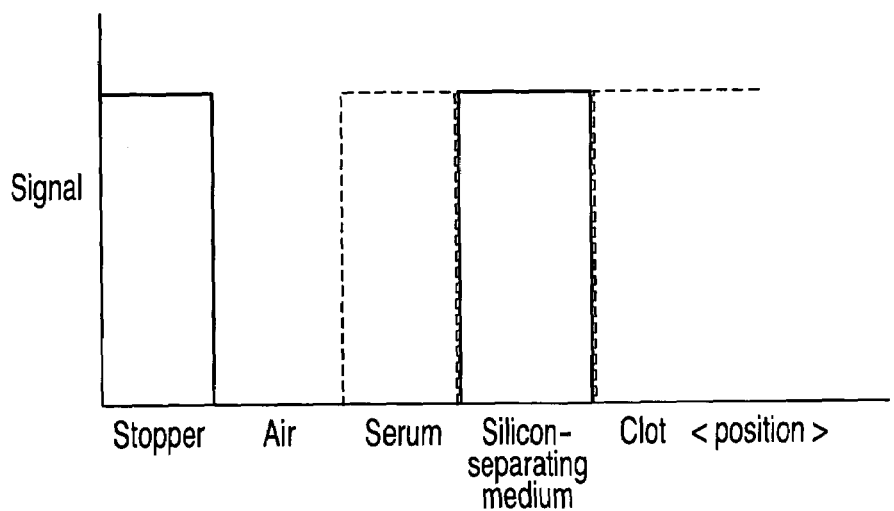
FIG. 5 is an illustration of position sensing signals that are supplied to an arithmetic unit from a reception element of each of the first and second sensing units.

As the first and second sensing units 11 and 12 move down, the reception elements 11b and 12b supply the arithmetic unit 15 with the signals for sensing the serum A, the clot C, the silicon-separating medium B, etc, as shown in FIG. 5. The driving motor 7 supplies the unit 15 with the position (height) sensing signal. The unit 15 processes these signals to calculate respective separation positions e, f and g of the blood sample in the test tube 1, respective separation ranges of height d of air height a of serum A and height b of silicon-separating medium B, and height h of the stopper 2, and stores these information items in the memory.

The above information items can be sensed as described above. If the sum of heights h, d and a is calculated, an amount of movement of the nozzle of an aliquot/pipette instrument can be obtained. If the serum A is aliquoted based on this amount of movement, the nozzle of the instrument can be prevented from contacting the silicon-separating medium B and sucking it up, and the serum A can be pipetted without remaining on the silicon-separating medium B.

Figure 3:
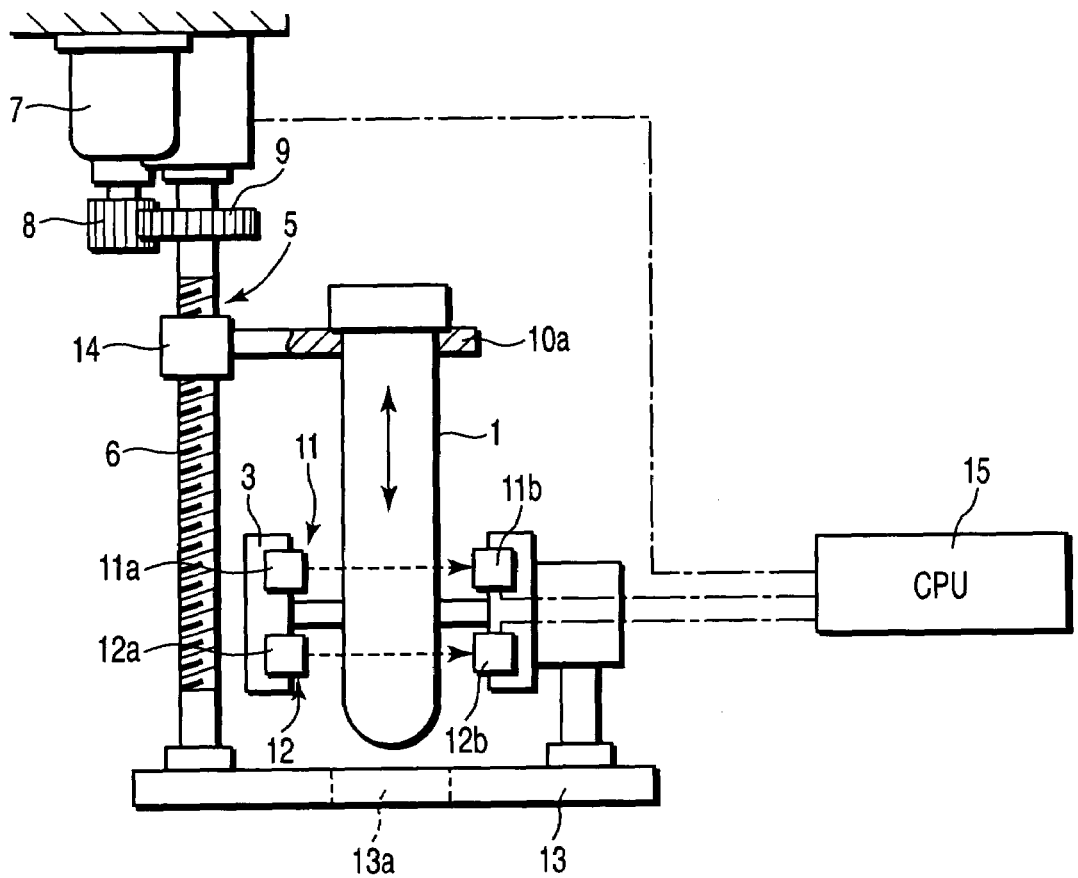
FIG. 3 is diagram showing a configuration of a sensing apparatus according to a second embodiment of the present invention, which senses a blood sample contained in a test tube.

FIG. 3 shows a blood sample sensing apparatus according to a second embodiment of the present invention. The sensing apparatus includes first and second sensing units 11 and 12. A test tube 1 and a holding arm 10a for holding the test tube 1 vertically are moved up and down by the same driving unit 5 as that of the first embodiment. The first and second sensing units 11 and 12 are fixed on a substrate 13. The test tube 1 stops in the uppermost position with its top end portion held by the holding arm 10a, and moves down through a hole 13a of the substrate 13. The holding arm 10a has a screw piece 14 into which a screw shaft 6 is inserted and moves up and down so as to slide along a vertical guide (not shown). Since the other components have the same configuration and function as those of the first embodiment, they are denoted by the same reference numerals and their detailed descriptions are omitted.

Figure 4:
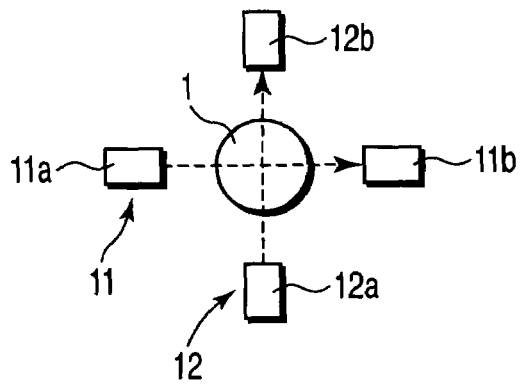
FIG. 4 is a schematic plan view of first and second sensing units that are arranged at the same level in the vertical direction of the test tube.

The first and second sensing units 11 and 12 can be changed in position to each other and, in other words, the second sensing unit 12 can be arranged higher than the first sensing unit 11. Furthermore, they can be arranged at the same level in the vertical direction of the test tube 1 such that their infrared ray radiation directions cross at right angles as shown in FIG. 4.

In the first and second embodiments, a test tube is used as a sample container. However, the sample container is not limited to the test tube. Another sample container can be used if it can contain a blood sample that can be sensed by the sensing apparatus. If a container exclusive to the sensing apparatus is manufactured or a sample container suitable thereto is selected, the apparatus can be increased in sensing accuracy and sensing speed.

Additional advantages and modifications will readily occur to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents. For example, the first and second sensing units 11 and 12 in the above embodiment merely output the sensing signals indicating whether or not the serum A, the clot C or the silicon-separating medium B is present between the infrared ray radiation element 11a or 12a and the infrared ray reception element 11b or 12b. Thus, the arithmetic unit 15 calculates the position of the serum A, the clot C or the silicon-separating medium B based on the sensing signals and the position (height) sensing signal from the driving motor 7. However, if the first and second sensing units 11 and 12 incorporate a position detecting function and receive the position (height) sensing signal from the driving motor 7, the first and second sensing units 11 and 12 can directly output the position of the serum A, the clot C or the silicon-separating medium B1 and the arithmetic unit 15 can be omitted.

What is claimed is:

1. An apparatus for sensing a blood sample contained in a sample container, the blood sample being separated into a serum and a clot by a separating medium, the apparatus comprising:
   a first sensing unit which senses the separating medium using an infrared sensor and outputs a first sensing signal;
   a second sensing unit which senses the serum and the clot using an infrared sensor and outputs a second sensing signal;
   a driving unit which moves the first sensing unit and the second sensing unit relative to the sample container;
   a position sensing unit which outputs a position sensing signal indicating a position of the first sensing unit and a position of the second sensing unit; and
   a controller which calculates positions of the separating medium, the serum and the clot in response to the first sensing signal, the second sensing signal and the position sensing signal.

2. The apparatus according to claim 1, wherein the infrared sensor of the first sensing unit includes:
   an infrared ray radiation element which radiates infrared rays toward the sample container; and
   an infrared ray reception element which receives infrared rays through the sample container and outputs the first sensing signal.

3. The apparatus according to claim 2, wherein the infrared ray radiation element of the first sensing unit radiates infrared rays whose wavelength ranges from 600 nm to 800 nm.

4. The apparatus according to claim 1, wherein the infrared sensor of the second sensing unit includes:
   an infrared ray radiation element which radiates infrared rays toward the sample container; and
   an infrared ray reception element which receives infrared rays through the sample container and outputs the second sensing signal.

5. The apparatus according to claim 4, wherein the infrared ray radiation element of the second sensing unit radiates infrared rays whose wavelength ranges from 1400 nm to 1700 nm.

6. The apparatus according to claim 1, wherein the sample container contains air between the serum and a stopper and the controller calculates positions of the stopper and air in response to the first sensing signal, the second sensing signal and the position sensing signal.

7. The apparatus according to claim 1, further comprising an extraction unit which extracts the serum from the sample container based on the positions of the separating medium, the serum and the clot, which are calculated by the controller.

8. The apparatus according to claim 1, further comprising a holding unit which holds the sample container with a bottom thereof downward,
   wherein the first sensing unit and the second sensing unit are arranged at different levels, and the driving unit moves up and down while keeping the first sensing unit and the second sensing unit at different levels.

9. The apparatus according to claim 1, further comprising a holding unit which holds the sample container with a bottom thereof downward,
   wherein the first sensing unit and the second sensing unit are arranged at a same level, and the driving unit moves up and down while keeping the first sensing unit and the second sensing unit at the same level.

10. A method of sensing a blood sample contained in a sample container, the blood sample being separated into a serum and a clot by a separating medium, used for a sensing apparatus having first sensing means for sensing the separating medium, second sensing means for sensing the serum and the clot and position sensing means for sensing a position of the first sensing means and a position of the second sensing means, the method comprising:
    sensing the separating medium by the first sensing means;
    sensing the serum and the clot by the second sensing means;
    sensing a position of the first sensing means and a position of the second sensing means by the position sensing means;
    calculating positions of the separating medium, the serum and the clot based on detection results of the first sensing means, the second sensing means and the position sensing means; and
    controlling processing of the blood sample based on the positions of the separating medium, the serum and the clot.

11. The method according to claim 10, wherein the sample container contains air between the serum and a stopper, the method further comprising:
    sensing the stopper by the first sensing means and sensing the air by the second sensing means; and
    calculating a position of each of the stopper and the air based on detection results of the first sensing means, the second sensing means and the position sensing means.

12. The method according to claim 10, wherein
    the separating medium sensing comprises radiating infrared rays whose wavelength ranges from 600 nm to 800 nm toward the sample container and receiving the infrared rays through the sample container.

13. The method according to claim 10, wherein the serum and clot sensing comprising irradiating infrared rays whose wavelength ranges from 1400 nm to 1700 nm toward the sample container and receiving the infrared rays through the sample container.

14. The method according to claim 10, further comprising extracting the serum from the sample container based on the positions of the separating medium, the serum and the clot.

* * * * *